(12) United States Patent
Mueller

(10) Patent No.: US 9,278,320 B2
(45) Date of Patent: Mar. 8, 2016

(54) DISSOLUTION CHAMBER FOR CLEANING TABLETS

(75) Inventor: Daniel Mueller, Burgstall (IT)

(73) Assignee: Dental Care Innovation GmbH, Nuremburg (DE)

( * ) Notice: Subject to any disclaimer, the term of this patent is extended or adjusted under 35 U.S.C. 154(b) by 254 days.

(21) Appl. No.: 13/520,703

(22) PCT Filed: Jun. 10, 2011

(86) PCT No.: PCT/IB2011/001324
§ 371 (c)(1),
(2), (4) Date: Jul. 5, 2012

(87) PCT Pub. No.: WO2012/069893
PCT Pub. Date: May 31, 2012

(65) Prior Publication Data
US 2013/0215705 A1    Aug. 22, 2013

(30) Foreign Application Priority Data

Nov. 12, 2010 (DE) .......................... 10 2010 051 225

(51) Int. Cl.
*B01F 5/00* (2006.01)
*A61C 3/025* (2006.01)
*B01F 1/00* (2006.01)

(52) U.S. Cl.
CPC ............... *B01F 5/0057* (2013.01); *A61C 3/025* (2013.01); *B01F 1/0033* (2013.01)

(58) Field of Classification Search
CPC .... B01F 5/0057; B01F 1/0033; B01F 1/0062; B01F 1/0027; A61C 2/025
USPC ......... 422/279, 277, 275, 274, 268, 266, 264, 422/263, 261

See application file for complete search history.

(56) References Cited

U.S. PATENT DOCUMENTS

| | | | |
|---|---|---|---|
| 1,664,369 A | 1/1925 | Maurer | |
| 2,814,877 A | 12/1957 | Tilden | |
| 3,863,628 A | 2/1975 | Vit | |
| 3,971,136 A | 7/1976 | Madsen | |
| 4,174,571 A | 11/1979 | Gallant | |
| 4,214,871 A | 7/1980 | Arnold | |
| 4,625,780 A * | 12/1986 | Burnham | 366/336 |
| 4,936,335 A * | 6/1990 | Macon | 422/261 |
| 4,965,968 A | 10/1990 | Kelsall | |
| 4,978,297 A | 12/1990 | Vlock | |
| 5,374,119 A * | 12/1994 | Scheimann | 366/165.5 |
| 5,810,999 A | 9/1998 | Bachand et al. | |
| 2003/0013063 A1 | 1/2003 | Goldman | |
| 2004/0125689 A1 | 7/2004 | Ehrfeld et al. | |

FOREIGN PATENT DOCUMENTS

| | | |
|---|---|---|
| DE | 3322716 A1 | 1/1985 |
| DE | 19729516 A1 | 1/1999 |
| DE | 10123093 A1 | 11/2002 |

(Continued)

OTHER PUBLICATIONS

International Search Report in corresponding PCT/IB2011/001324, Nov. 29, 2011, 3 pages.

*Primary Examiner* — Tony G Soohoo
(74) *Attorney, Agent, or Firm* — Hooker & Habib, P.C.

(57) ABSTRACT

In order to dissolve cleaning tablets in a constant stream of media, a rinsing out chamber is suggested, in which the tablet is dissolved in an upward rotary stream of the medium, that keeps it afloat against a filter mesh.

20 Claims, 1 Drawing Sheet

(56) References Cited

FOREIGN PATENT DOCUMENTS

| DE | 69605184 T2 | 5/2005 |
| DE | 102004062076 A1 | 7/2006 |
| DE | 102007058112 A1 | 6/2009 |
| WO | 2007110710 A2 | 10/2007 |
| WO | 2008004650 A1 | 4/2008 |
| WO | 2008046580 A1 | 4/2008 |
| WO | 2011070385 A1 | 6/2011 |

* cited by examiner

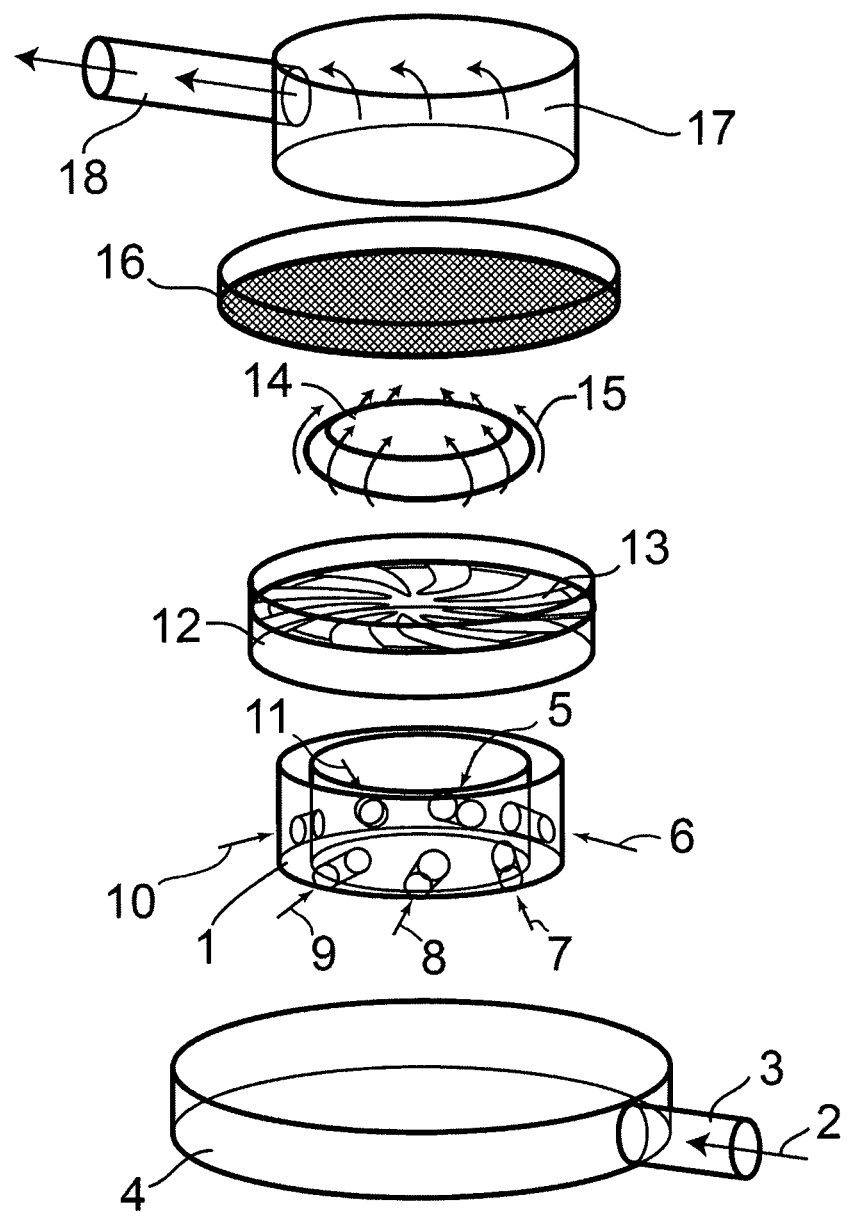

DISSOLUTION CHAMBER FOR CLEANING TABLETS

FIELD OF THE INVENTION

The invention refers to a dissolution chamber for tablets, as for adding cleaning agents, nutrients, fertilizers, or biocides to a stream of water or other solvents.

BACKGROUND OF THE INVENTION

For cleaning equipment, or in irrigation systems and disinfection devices, water or other media are mixed with additives, that are compacted to form a tablet. These use to be dissolved in a mixing chamber.

However, the dissolution of tablets hitherto can only be achieved with large quantities of water or solvent. Since the amount of material that is carried away in the medium decreases, the cleaning effect declines with the reduction of the tablet size. In the end, much water or other solvent must be spent for complete dissolution, without adequate cleaning effect. Therefore the process is often interrupted beforehand, so that a remainder of the tablet remains in the dissolution chamber, which sometimes is tedious to remove.

Another reason for annoying cleaning procedures is, that turbulences in the stream through the dissolution chamber lead to active and neutral zones, where the material easily deposes at walls and in corners.

This pertains particularly to cleaning agents with abrasive components, which are usually water insoluble and heavier and therefore are prone to deposition in partitions with low flow rate, mostly with applications, in which rather tight nozzles must be applied for to achieve an appropriate cleaning effect, because of then only a comparatively small flow speed arrives at high pressure.

For a such kind of applications—e.g. tooth cleaning with removal of plaque—a larger number of proposals have been made for cleaning agents containing abrasive particles.

PRIOR ART

The majority of the suggested solutions refer to the use of compressed air: either powdered blast grains are blown directly onto the teeth, or injected into a stream of water to be coated or mixed with it, or a cleaning mixture with blast grain (so-called slurry) is applied to dental surfaces with compressed air.

For dental practices these techniques are common, because there compressed air is regularly at hand for drills and blowing out devices.

However, for everyday dental hygiene with removal of biofilms and plaques the use of a compressor seems odd and would come at disproportionately high cost.

Nevertheless it is well known, that biofilms and deposits are only roughly removed with a toothbrush and therefore it is obvious, that daily cleaning with gently abrasive means is preferable, particularly since the surface of smooth teeth give a more pleasant and hygienic feel when touched with one's tongue.

For this purpose the employment of abrasive means in oral irrigators would be obvious—but this is, where the above mentioned problems arise.

Thereon a multiplicity of solutions had been presented, which however could not achieve acceptance so far:

Early proposals, like DE 197 29 516 A1, U.S. Pat. Nos. 1,664,369 2,814,877, 3,971,136, 3,863,628, as well as US 2003/0013063 A1, U.S. Pat. Nos. 4,214,871 and 4,174,571 refer to the use of pastes and powders, the mixing of which into a water jet is comparatively simple.

But these approaches failed commercially, as cleaning and refilling of the containers turned out to be quite cumbersome and cartridge systems tended to be blocked by agglomerations of insoluble media. Starting from the seventies of last century, therefore replaceable inserts were offered, such as tablets or caps.

Thus in DE 3322716 A1 a rod of preservative agent is suggested, that is rinsed along its long sides. However, increased thinning of the shank in its center often leads to its early break-down with consequent blockage of the nozzle and/or filters.

A mouth rinsing device of Gilette S.A. (DE 696 05 184 T2) with tubular caps, offered briefly on the market in the USA, exhibited similar problems, although similar rinsing out devices for garden hoses had quite worked satisfactory, while its larger nozzles permit rinsing out of rougher components, as long as they do not bloc the nozzle gap.

But this does not work with abrasive and insoluble components. Therefore the erosion of the caps and their breaking apart here led as well to a blockage of the discharge orifices.

An opposite problem appears with the solution on WO 2008/046580 A1 to Gimelli, where the tablet is positioned in an embracing housing against the direction of the water flow. It therefore cannot break apart, however inevitably neutral zones develop: here again residual substrates are intricately to be removed before a new tablet can be used.

Problem to be Solved

The task of the here disclosed, invention therefore is, to design a dissolution chamber for tablets—the simplest form of a compact preparation of cleaning agents—in such a way, that these effects cannot occur.

Problem Approach—Inventive Step

The inventive step is the idea to manage a uniform circulation of water under the tablet, that therefore is less affected from stronger erosion on the rim of its outer layers, and to avoid that it breaks up in the final phase. This is achieved with a hydrodynamically shaped dissolution chamber, wherein a coerced vortex keeps the tablet horizontally afloat.

SUMMARY OF THE INVENTION

The dissolution chamber for detergent tablets is designed in a way, that the incoming stream of water is first shifted into upstream turbulence by a centrifugal element, that lifts the tablet from a holding bracket against a filtering mesh, that covers the outlet above.

The distance between brackets and mesh must not be more than one quarter of the diameter plus the thickness of the tablet, so that the tablet cannot turn laterally, even when fairly ablated.

The brackets preferably consist of spiral fingers, whereon the tablet it is laid up. The whirling surge and the degassing of chemical contents from the tablet induces vibration, that provokes its rotation between the spiral fingers an the mesh until the entire surface is quite evenly ablated.

This way it is secured, that a constantly decreasing erosion of the components of the tablet can be accomplished.

This may be complemented by a multi-layer tablet composition of progressively softer, more easily ablating coatings (as described in our application DE 10 2010 051 226.5)—so not only to ablate a constant magnitude of active agents, and in the end to dissolute the tablet completely with a high concentration of hygroscopically swelling ingredients.

PREFERRED EMBODIMENT

In a preferred embodiment the water intake is directed through circular, inwardly converging orifices into a center bore, where it results in an upward torrent. The tablet, rested on finger-like brackets halfway up in this center bore is set afloat against a filter mesh above, that separates the cylindric bore from the duct of the outlet chamber, which leads through a hose into the nozzle.

DETAILED DESCRIPTION OF THE INVENTION IN DRAWINGS

The preferred embodiment of the system is illustrated by following drawing:

FIG. 1 demonstrates, how the water or medium jet 2 enters through the lower connecting stub 3 into the supply segment 4 of the dissolution chamber 1, where it is forced into turbulent motion by a centrifugal element 5 through its diagonal inlet bores 6 to 11 to the centrifugal chamber 12, on whose finger shaped brackets 13 the cleaning tablet 14 is placed.

The water stream 15, this way forced to carry it afloat, dissolves the tablet prior from its down side and gives it a lift up to the filter mesh 16 for holding it there, whereby the small gap 17 between brackets 13 and mesh 16 avoids, that it laterally turns or breaks.

The water stream, then containing the dissolved and the now released abrasive particles, enters into the transfer chamber 18 and from there into the connecting stub 19, which is the discharge opening.

What is claimed is:

1. A dissolution chamber for dissolving an abrasive cleaning tablet in a flow of liquid, the dissolution chamber comprising:
   a body defining a chamber, the body comprising an inlet into the chamber and an outlet out of the chamber spaced in a downstream direction from the inlet;
   a first stop in the chamber and a second stop in the chamber spaced downstream from the first stop, the first and second stops disposed to only partially obstruct the flow of liquid through the chamber and defining a central portion of said chamber for receiving a tablet therein;
   the first and second stops configured to retain between them a disk-shaped tablet that is sized to substantially obstruct flow of liquid through the chamber if the tablet were placed in the central portion of the chamber; and
   a flow guide fluidly disposed between the inlet and the first stop, the flow guide comprising an outer wall being disposed to obstruct flow from the inlet and a plurality of bores extending through the flow guide, each bore defined by a solid bore wall extending from the outer wall to a discharge opening in fluid communication with the central portion of the chamber, the bores being cooperatively aligned with one another to impart rotary motion to liquid discharged from the bores and flowing downstream to the first stop.

2. The dissolution chamber of claim 1 wherein the flow guide is a tubular member surrounding a central opening, the bores discharging into the central opening.

3. The dissolution chamber of claim 1 in combination with a generally disk-shaped tablet in the central portion of the chamber, the tablet when undissolved having a width dimension and a thickness dimension transverse to the width dimension, the distance between the first and second supports not more than the sum of one-quarter the width of the tablet plus the thickness of the tablet.

4. The dissolution chamber of claim 3 wherein the tablet is a multi-layer tablet having layers of different softnesses.

5. The dissolution chamber of claim 1 in combination with a source of liquid wherein the inlet is connected to the source of liquid and receives liquid having a pressure of between 4 bar and 10 bar.

6. The combination dissolution chamber and liquid source of claim 5 wherein liquid is being discharged from the dissolution chamber and impinges against a tooth of a human being.

7. The dissolution chamber of claim 1 wherein the second stop is a mesh extending across the chamber.

8. The dissolution chamber of claim 1 wherein the outer wall of the flow body is a substantially circular wall extending around an axis, the bores extending radially away from the axis.

9. A dissolution chamber for dissolving an abrasive cleaning tablet in a flow of liquid, the dissolution chamber comprising:
   a body defining a chamber, the body comprising an inlet into the chamber and an outlet out of the chamber spaced in a downstream direction from the inlet,
   first stop in the chamber and a second stop in the chamber spaced downstream from the first stop, the first and second stops disposed to only partially obstruct the flow of liquid through the chamber and defining a central portion of said chamber for receiving a tablet therein;
   the first and second stops configured to retain between them a disk-shaped tablet that is sized to substantially obstruct flow of liquid through the chamber if the tablet were placed in the central portion of the chamber; and
   a flow guide fluidly disposed between the inlet and the central chamber, the flow guide being configured to impart vortexal flow to all the liquid flowing downstream past the flow guide; and
   the flow guide comprising a body and bores extending through the body in series with the inlet, the bores angled and not parallel to the downstream direction of flow.

10. The dissolution chamber of claim 9 wherein the flow guide body extends along a vertical axis and the bores run horizontally and vertically at a 45 degree inclination to the axis.

11. The dissolution chamber of claim 9 in combination with a source of liquid wherein the inlet is connected to the source of liquid and the source of liquid supplies liquid having a pressure of between 4 bar and 10 bar.

12. The combination dissolution chamber and liquid source of claim 11 comprising liquid being discharged from the dissolution chamber and impinging against a tooth of a human being.

13. The dissolution chamber of claim 9 wherein the second stop is a mesh extending across the chamber.

14. A dissolution chamber for dissolving an abrasive cleaning tablet in a flow of liquid, the dissolution chamber comprising:
   a body defining a chamber, the body comprising an inlet into the chamber and an outlet out of the chamber spaced in a downstream direction from the inlet,
   a first stop in the chamber and a second stop in the chamber spaced downstream from the first stop, the first and second stops disposed to only partially obstruct the flow of liquid through the chamber and defining a central portion of said chamber for receiving a tablet therein;

the first and second stops configured to retain between them a disk-shaped tablet that is sized to substantially obstruct flow of liquid through the chamber if the tablet were placed in the central portion of the chamber; and a flow guide fluidly disposed between the inlet and the central chamber, the flow guide configured to impart vortexal flow to liquid flowing downstream past the flow guide, the flow guide comprising spiral fingers.

15. The dissolution chamber of claim 14 wherein the first support comprises upstream-facing surfaces on said spiral fingers.

16. The dissolution chamber of claim 14 wherein the flow guide body extends along a vertical axis and the bores run horizontally and vertically at a 45 degree inclination to the vertical axis.

17. The dissolution chamber of claim 14 in combination with a generally disk-shaped tablet in the central portion of the chamber, the tablet when undissolved having a width dimension and a thickness dimension transverse to the width dimension, the distance between the first and second supports not more than the sum of one-quarter the width of the tablet plus the thickness of the tablet.

18. The dissolution chamber of claim 14 in combination with a source of liquid wherein the inlet is connected to the source of liquid and the source of liquid supplies liquid having a pressure of between 4 bar and 10 bar.

19. The combination dissolution chamber and liquid source of claim 18 comprising liquid being discharged from the dissolution chamber and impinging against a tooth of a human being.

20. The dissolution chamber of claim 9 in combination with a generally disk-shaped tablet in the central portion of the chamber, the tablet when undissolved having a width dimension and a thickness dimension transverse to the width dimension, the distance between the first and second supports not more than the sum of one-quarter the width of the tablet plus the thickness of the tablet.

* * * * *